United States Patent [19]
Russo

[11] Patent Number: 6,165,168
[45] Date of Patent: Dec. 26, 2000

[54] CLOSED SYSTEM ADAPTER FOR CATHETERS

[76] Inventor: Ronald D. Russo, 8 Candleberry Rd., Barrington, R.I. 02806

[21] Appl. No.: 09/143,763

[22] Filed: Aug. 31, 1998

Related U.S. Application Data

[60] Provisional application No. 60/057,311, Sep. 2, 1997.

[51] Int. Cl.[7] ................................................. A61M 25/16
[52] U.S. Cl. ......................... 604/533; 604/247; 604/256
[58] Field of Search .................................. 604/533, 169, 604/247, 250, 256, 270, 33, 34, 905

[56] References Cited

U.S. PATENT DOCUMENTS

| | | | |
|---|---|---|---|
| 5,549,657 | 8/1996 | Stern et al. | 604/283 |
| 5,578,059 | 11/1996 | Patzer | 604/249 |
| 5,716,347 | 2/1998 | Gibbs et al. | 604/247 |
| 5,718,691 | 2/1998 | Russo | 604/247 |
| 5,720,734 | 2/1998 | Copenhaver et al. | 604/247 |
| 5,792,112 | 8/1998 | Hart et al. | 604/167 |

*Primary Examiner*—Wynn Wood Coggins
*Assistant Examiner*—Kevin C. Sirmons
*Attorney, Agent, or Firm*—Robert J. Doherty

[57] ABSTRACT

A closed system adapter for catheters is disclosed. The adapter comprises a rigid outer housing having an inlet end with an internal cavity, and outlet end with a central passageway, the outlet end having a series of incrementally larger diameter steps permitting connection to various sized catheters.

Positioned within the inlet end internal cavity is a resilient valve member normally biased to a sealed closed position. The valve member includes a generally cylindrical wall with a diaphragm with a pre-slit partitioned across the wall. The cylindrical wall dimensioned to be slightly larger in diameter than the inlet end cavity of the housing except for a recessed area where the diaphragm is positioned. The cylindrical wall providing inward compressive force except in the recess area permitting the diaphragm to remain in a steady state normally closed position without excessive inwardly compressive force.

8 Claims, 6 Drawing Sheets

CLOSED SYSTEM ADAPTER FOR CATHETERS

This application claims the benefit of U.S. Provisional Application No. 60/057,311, filed Sep. 2, 1997.

BACKGROUND OF THE INVENTION

This invention relates to medical devices and particularly to an adapter which can be directly connected to a wide variety of catheters especially long term feeding and medicating catheters such as gastrostomy tubes, jejunal tubes, nasogastric tubes, or stomach tubes.

These types of catheters or feeding tubes as they are called, are needed to provide long term enteral nutrition to the patient. Typically, the patient can be fed by a choice of three methods of enteral nutrition: delivery by means of bolus feeding, pump feeding, or gravity feeding. Attached to the feeding tube is usually a connector with a plug cap or a flip cap which seals off the catheter when the patient is not being fed. The flip cap often comes off or leaks permitting loss of stomach contents out the tube. In addition, the pump and gravity methods use delivery sets which can be connected to the tube for hours to deliver continuous enteral nutrition while the patient sleeps. Disconnection of the delivery set is a common problem and bulky pinch clamps are often used because the flip caps fail so often.

Feeding tubes usually protrude from the body about 6 to 10 inches and are sometimes left in place up to a year or longer since they are manufactured from inert, biocompatible silicone or polyurethane. Feeding can take place up to three to six times a day.

Many of the enteral delivery sets have rigid plastic connectors with gripping barbs or steps which tend to destroy or ruin the various attempts at check valves used in feeding tubes. U.S. Pat. No. 4,944,732 describes one such device but this is limited to a low profile Gastro-Port from Sandoz Nutrition Corp. Recently Wilson-Cook Medical, Inc. has commercially introduced the Passport low profile gastrostomy device which functions similar to the Gastro-Port, but has a circular valve.

The circular valve structure of the Wilson-Cook Passport is described in detail along with relevant prior art in U.S. Pat. No. 5,718,691 to Russo and U.S. Pat. No. 5,716,347 to Gibbs et. al. The Gibbs et. al. U.S. Pat. No. 5,716,347 utilizes the circular valve structure of U.S. Pat. No. 5,718,691 to Russo. The circular valve to Russo uses a structure similar to the present invention. However, the Russo circular valve has a rigid outer wall portion which applies direct inward compressive force on the inner slit diaphragm. While the circular valve of Russo has proven to be an excellent clinical device, this direct compressive force sometimes can result in misalignment or mismatch of the valve slit opening permitting slight backflow leakage out the valve, especially when barbed connectors are repeatedly used. In addition, the Russo valve requires a separate retainer cap which leaves an internal crevice, joint, or seam between the cap and the circular valve, which can accumulate enteral formula which could prematurely clog the entrance way to the valve if it is not flushed according to instructions. The present invention is considered to be an improvement over the Russo circular valve in that the valve of the present invention eliminates the slight backflow, reduces the need for meticulous flushing and nursing care and extends the indwelling longevity of the device.

Other valve structures for catheter ports are shown in the prior art in the Bodai U.S. Pat. No. 4,351,328 and the hemostasis valve of Guest U.S. Pat. No. 5,000,745 and the valve of Suzuki U.S. Pat. No. 4,673,393. These devices are adequate for their intended short term use, but would not prove to be reliable over long term or repeated connection and disconnection use.

Other general medical art valves include U.S. Pat. Nos. 3,853,127 to Spademan; 4,430,081 to Timmermans; 5,114,408 to Fleishhaker et. al.; 5,125,903 to McLaughlin et. al.; and 5,261,885 to Lui.

U.S. Pat. No. 5,279,571 to Larkin discloses a self-sealing valve with a non-interference fit within its rigid housing which is contrary to the present invention. U.S. Pat. No. 5,167,637 to Okada et. al. is also a short term hemostatic valve, and U.S. Pat. No. 5,336,203 to Goldhardt is also a low profile gastrostomy device with a valve included as part of its structure.

All of the above devices are designed for either hemostatic access sites, parenteral injection sites, or low profile gastrostomy ports with limitations. None provide a universal, one size fits all type catheter adapter which can directly connect to a wide variety of catheters and can accept all delivery sets whether pump or gravity as well as directly connect to a bolus 60 cc syringe.

The present invention is directed to a low cost closed system adapter for long term use with indwelling catheters with advantages over the previously described devices.

SUMMARY OF THE INVENTION

The adapter of the present invention provides a plug in adapter for use in long term indwelling catheters with an improved one-way entrance valve which will remain positively sealed closed after repeated and extensive use. The valve is uniquely designed to prevent back leakage through the valve after the repeated insertions of delivery set tips which is required during the long term care of patients needing enteral nutrition.

The present invention includes a rigid outer housing having an inlet, an outlet end with an central passageway. A cavity having generally parallel inner side walls is located at the inlet end of the housing. A resilient self sealing valve member is positioned in the cavity. The valve member has a diaphragm portion which has a through slit therein and outer sidewalls which generally conform in shape to the cavity, but are larger in dimension than the cavity when uncompressed except most importantly in the outer peripheral edge area of the diaphragm.

The valve member is compressively fitted within the cavity such that the inner sidewalls press inwardly on the outer sidewalls of the valve member both above and below the diaphragm but not on the outer peripheral edge of the diaphragm. These compressive forces both above and below the diaphragm permit the diaphragm to be in a steady state of equilibrium without excessive inward pressure which tends to buckle or warp the slit permitting mismatch of the slit opening with resultant leakage back through the valve. The diaphragm is permitted to flex slightly outward and inward during insertion of a delivery set or syringe tip. After removal of the tip, the diaphragm will automatically reseat itself back to its original position wherein the slit is perfectly aligned back to its original position. The resilient valve member includes a molded in "o" ring located above the diaphragm which acts as a positive entrance seal on the delivery set tip. The "o" ring is also compressively fitted within the inner sidewalls of the cavity preventing the "o" ring from stretching or deforming during repeated insertions of the delivery tip.

In the preferred embodiment the cross sections of the housing and the valve member are circular. The housing outlet end has a stepped outer connector portion which permits connection of the adapter to a wide variety of long term indwelling catheters typically from 16 fr up to 30 fr in size and the connector portion has an inner passageway or tapered inner bore exiting at an outlet end opening.

A closure cap with a central opening is positioned on top of the inlet on the housing which positively locks the valve member in place within the cavity. The cap is fixed onto the inlet.

The valve can be uniquely designed to be incorporated into a low profile gastrostomy device to completely eliminate the separate closure cap and to provide a seamless internal configuration of the valve to reduce internal clogging or enteral formula build-up.

Accordingly, it is a primary object of the present invention to provide a closed system enteral feeding adapter which can directly connect to a wide variety of different size catheters.

Another object of the present invention is to provide an enteral adapter with an improved one-way entrance seal which prevents back flow through the entrance seal.

Another object of the present invention is to provide a closed system enteral adapter which can be easily removed and replaced with a new adapter in a wide variety of catheters.

Another object of the present invention is to provide a closed system enteral adapter which can be assembled and manufactured inexpensively.

Another object of the present invention is to provide a device which can easily convert any open catheter to a closed system device.

Another object of the present invention is to provide an improved low profile gastrostomy feeding device with an improved entrance seal and anti-reflux valve.

Other advantages, objects, and features of the present invention will become readily apparent from the following detailed description of the invention, from the claims, and from the accompanying drawings.

DESCRIPTION OF THE PREFERRED EMBODIMENT

In order to understand the details of the invention, the specifics will be discussed in the embodiments described.

Figure 1:
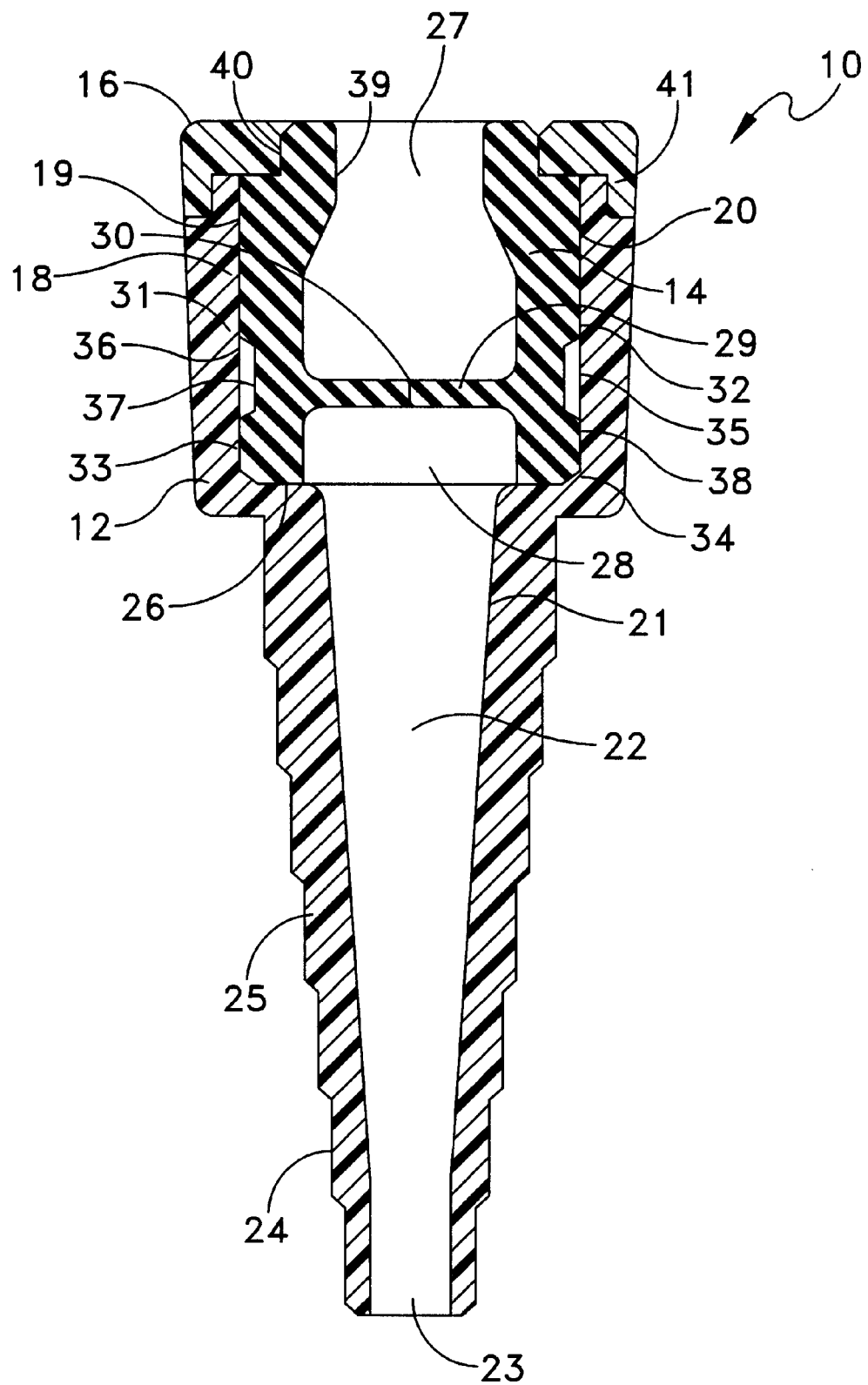
FIG. 1 is a full cross sectional view of the assembled closed system adapter.

Turning now to FIG. 1 there is illustrated the preferred embodiment of closed system adapter 10 which includes rigid injection molded housing 12, resilient valve member 14, and rigid injection molded sealing cap 16. Housing 12 is molded in one-piece of polycarbonate plastic but could be molded from other rigid thermoplastics. Housing 12 includes an inner circular cavity 18 which is 0.50 inches in inner diameter with parallel inner sidewalls 19 and 20. Centrally connected to cavity 18 is inner passageway 21 which has a tapered bore 22 terminating at an outlet end 23. Outside of tapered bore 22 is a series of gradually increasing steps 24 which form a stepped connector portion 25. These steps will permit plug in connection to a wide variety of catheters from 16 fr up to 30 fr.

Valve member 14 is typically molded from medical grade silicone about 50 shore durometer in one piece. Valve member 14 has an upper entrance opening 27 and a lower exit opening 28. Partitioned across both openings is diaphragm 29 which has a wall thickness of about 0.050 inches with a centrally located pierced slit 30. Valve member 14 has cylindrical upper outer walls 31 and 32 located above diaphragm 29 and cylindrical lower outer walls 33 and 34 located below diaphragm 29.

All outer walls on valve member 14 have an outer diameter about 0.015 to 0.025 inches larger than inner walls 19 and 20 within the cavity 18 such that when valve member 14 is press fit into cavity 18, inner walls 19 and 20 exert an inward compressive force on outer walls 31, 32, 33, and 34 of the valve member 14 both above and below diaphragm 29.

However, and most importantly, molded between outside walls 31, 32, and 33 and 34 is cylindrically recessed portion 35 and 36 located outboard and on the outer peripheral edge of diaphragm 29. As such, inward compressive force is only exerted above and below diaphragm 29 such that diaphragm 29 remains in a steady state of resilient equilibrium. Outer recessed walls 37 and 38 are thus permitted to flex outward and inward depending upon whether slit 30 is either opened or closed. This steady state of equilibrium of the diaphragm permits the slit 30 to automatically reposition itself to perfect sealing realignment to seal lower exit opening 28 to prevent any reflux back up into upper entrance opening 27. Therefore, the diaphragm 29 can be repeatedly opened hundreds of times and will return to its normally biased sealed closed position once the diaphragm 29 is closed.

Integrally molded into valve 14 is entrance opening 27 which has a molded in "o" ring 39 which acts as the sealing surface for a delivery set tip. As shown, walls 19 and 20 exert a slight inward compressive force to prevent "o" ring 39 from stretching outward to prevent leakage.

Closure cap 16 also has an inner opening 40 which also exerts a slight inward compressive force to prevent stretching at the very opening or "o" ring 39. Closure cap 16 has a lap joint with housing 12 such that the cap can be easily ultrasonically welded to housing 12 to seal in valve member 14 since cap 16 is also molded of polycarbonate. The entire assembly then consists of only three components: the housing 12, the valve member 14, and closure cap 16.

Figure 2:
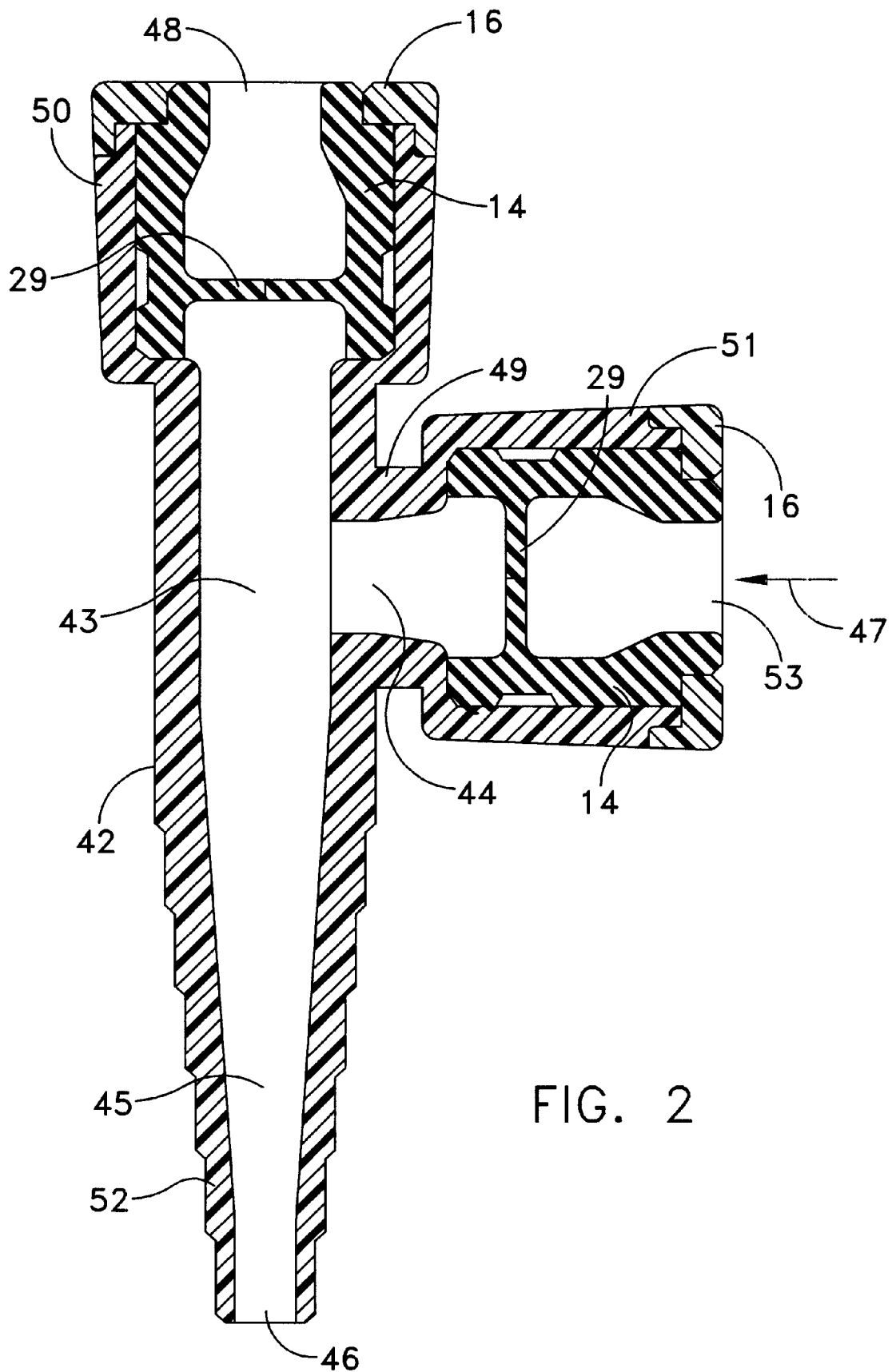
FIG. 2 is a full cross sectional view of an alternate embodiment of the assembled closed system adapter including a closed system side port.

FIG. 2 depicts an alternate embodiment which includes a side port 47 which permits in line flushing or administration of crushed and dissolved medication into the catheter while continuous feeding delivery is taking place through main opening 48. Continuous delivery of enteral formula requires a very slow continuous drip of formula into the patient over an extended period of time usually 6 to 10 hours. During that time it is often desirable to flush the catheter to prevent clogging or to administer medications. The use of a side port would permit in-line flushing without having to disconnect the delivery set. As such, FIG. 2 shows side-port 47 with rigid molded outer housing 42 with molded in side stem 49. Housing 42 has a main outer housing 50 and a side stem outer housing 51. Press fit into both housings is previously described valve member 14. Closure cap 16 seals in place valve member 14 in both housings as shown.

Main housing 42 includes a main fluid flow passage 43 which continues into tapered bore 45 and out outlet 46 in fluid communication with passage 43 is side stem passage 44. Once stepped portion 52 on housing 42 is connected to the catheter the embodiment of FIG. 2 will now provide two closed system openings through main opening 48 and side port opening 53. Both openings are normally sealed closed by valve member 14 but both openings can be used simultaneously or individually depending upon preference. Therefore, clamps on the tube are not needed, and there are no caps to break off or pop off. Both openings 48 and 53 have a long life expectancy and either port can accept pump, gravity, bolus, or irrigation syringes, because both valve members 14 are normally biased sealed closed.

Figure 3:
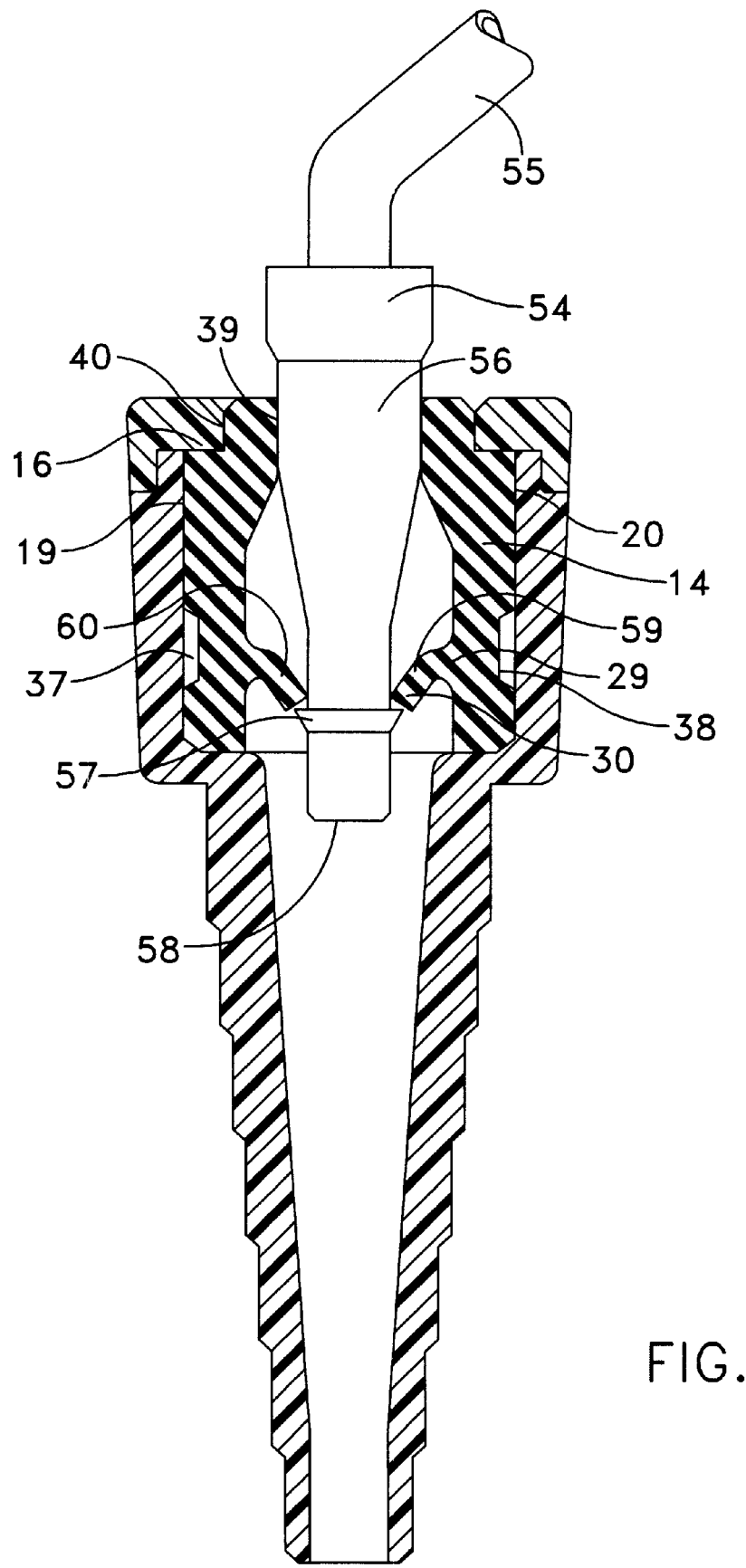
FIG. 3 is a full cross sectional view of the adapter depicted in FIG. 1 showing the insertion of a delivery tip into the adapter.

FIG. 3 depicts the preferred embodiment of FIG. 1 only with a typical delivery set tip 54 manually inserted and engaged with valve member 14. Delivery set tip 54 is attached to tubing line 55 which administers liquid enteral formula. The tip 54 usually has a tapered rearward end 56 and a frontal barb or stepped portion 57 which terminates in exit opening 58. After manual insertion of tip 54 into valve member 14 tapered rearward end 56 will compressibly engage and seal on "o" ring 39 which exerts an inward compressive force from inner walls 19 and 20 and also from inner opening 40 on closure cap 16. Barb 57 will splay open slit 30 on diaphragm 29 to form two leafs 59 and 60 on diaphragm 29, but once the barb 57 is retracted after removal of tip 54 recess 37 and 38 permit the diaphragm 14 to snap back into perfect realignment such that slit 30 reseats itself positively closed without any mismatch of slit opening 30 to prevent any leakage or backflow.

The valve member 14 can be repeatedly used for hundreds of times without any back leakage of stomach fluid out the adapter, since the valve member 14 works automatically to both open and close. The healthcare professional is protected from contact with leaking body fluids which could pose a health hazard. Also, outside contamination is prevented from entering the catheter which also protects the patient from outside infections. Once the adapter of the present invention is plugged into the indwelling catheter it converts the open catheter into a closed system catheter. The adapter can remain with the catheter for the life of the catheter or can be periodically removed from the catheter and replaced with a new one if desired.

Figure 4:
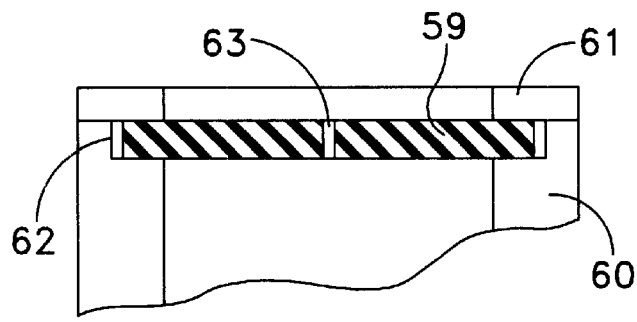
FIG. 4 is a partial cross sectional view of a typical prior art diaphragm type valve.
Figure 5:
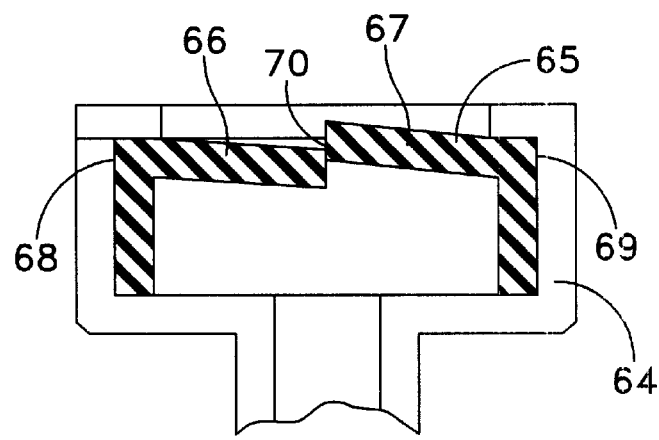
FIG. 5 is also a partial cross sectional view of another prior art diaphragm type valve.

By way of comparison, FIGS. 4 and 5 depict the typical prior art diaphragm type valves. FIG. 4 shows the hemostasis valve of Larkin in U.S. Pat. No. 5,279,571 consisting of valve 59 positioned in housing 60. This type of valve need only function for a short period of time since it is usually used as an access site for parenteral fluid delivery, typically for several hours or days. The valve is held in downward compressive force by cap 61. There is no radial or inward compressive force permitted on the valve and usually there is a slight gap 62 left. In the Larkin patent this type of valve is asserted to reduce kickback of an inserted instrument into the valve but after repeated insertions of an instrument slit opening 63 will stretch open wherein leakage will occur after a dozen or so insertions. By comparison FIG. 5 depicts the type of circular valve used in the Wilson-Cook Passport low profile gastrostomy tube to prevent fluid reflux and is the circular valve of prior art U.S. Pat. No. 5,718,691 to Russo which repeatedly asserts the requirement of inward compressive force directly on the leafs of the inner diaphragm valve in order for the circular valve to function properly.

This type of valve is better at long term prevention of reflux, however, the leafs 66 and 67 of diaphragm valve 65 are prone to slight mismatch especially when a barbed connector fitting is removed from the valve. Valve 65 is press fit into compression collar 64 such that inner walls 68 and 69 exert an inward compressive force directly on valve 65. This inward compressive force on leafs 66 and 67 can possibly result in buckling and mismatch of slit opening 70. Slit opening 70 thus has a tendency not to reseat itself permitting slight leakage to backflow through the valve, especially after repeated insertions of a barbed connector fitting through the valve. Often, the leafs 66 and 67 need to be manually reseated by inserting a cotton type swab. Also, this type of valve requires preconditioning with silicone grease to reduce drag at the slit opening 70. These two comparisons are presented to show the advantages of the valve 14 used in the present invention.

Figure 6:
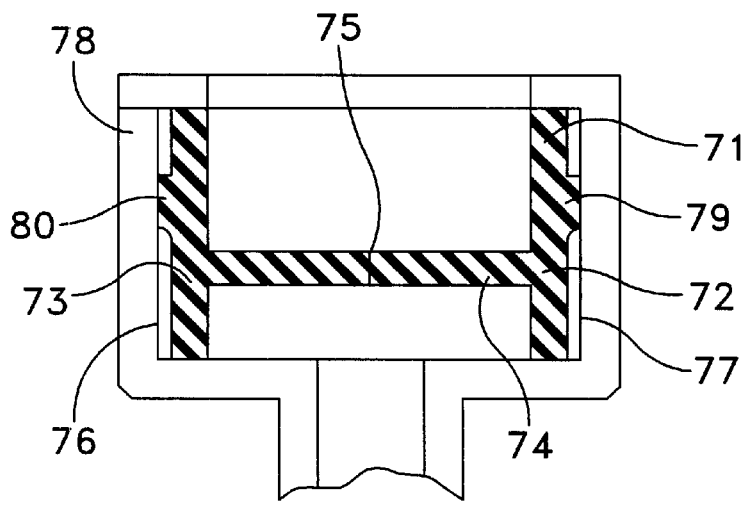
FIG. 6 is a partial cross sectional view of an alternate embodiment of the valve of the present invention.

FIG. 6 shows an alternate embodiment of valve 14 shown in FIG. 1. Valve 71 is very similar to previously described valve 14 in that it also has outer walls 72 and 73 and diaphragm 74 and slit 75, but outer walls 72 and 73 do not contact inner walls 76 and 77 on rigid outer housing 78. Molded into outer walls 72 and 73, just above diaphragm 74 is annular ring 79 and 80 which provides inward compression just above diaphragm 74. Diaphragm 74 is permitted to flex inward and outward with similar action to the preferred embodiment shown in FIG. 1. A second annular ring can also be located below the diaphragm 74 if desired. As such, one can design a valve with inward compressive force either singularly above or below the diaphragm, or one can choose to have compressive force both above and below the diaphragm as described in the preferred embodiment of FIG. 1. The most important element, however, is that no inward compressive force must take place in the diaphragm area located at its outer peripheral edge as is the case with the circular valve of prior art U.S. Pat. No. 5,718,691 to Russo.

In addition, the unique valve structure of resilient valve member 14 can be located as part of housing 12 in inner cavity 18 without its stepped connector portion 25 and can form the basis of a valve module which can be placed in any kind of access port for a catheter, be it a singular port or a side port embodiment.

Figure 7:
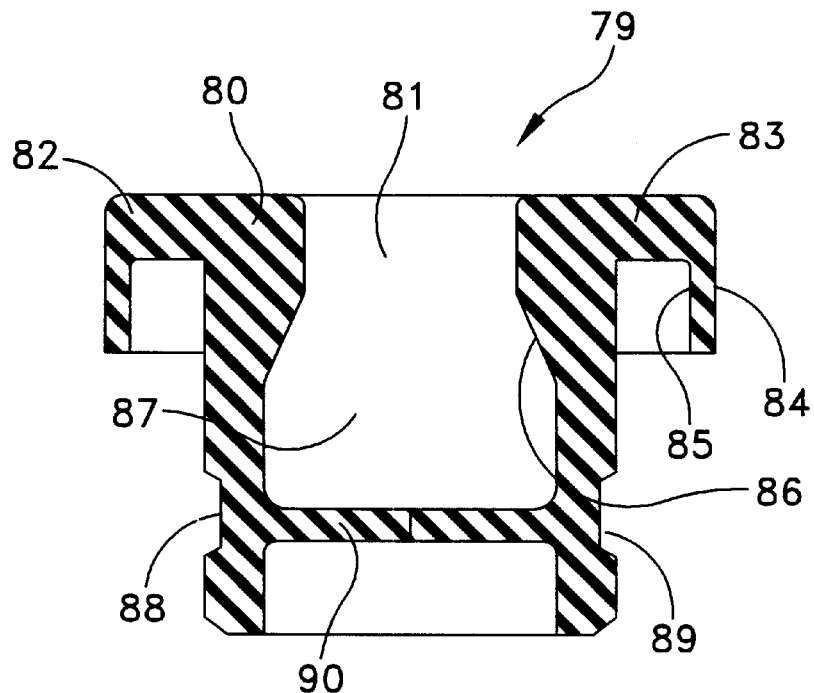
FIG. 7 is a full cross sectional view of an alternate embodiment of the resilient valve member.

FIG. 7 shows an alternate embodiment of valve 14 shown in FIG. 1. Valve 79 has an identical diaphragm slit valve. However, it clearly depicts a seamless internal structure wherein cap 80 is now molded integral and part of valve 79. Cap 80 extends outward from entrance 81 on both sides 82 and 83 and terminates in downward flange 84 having inner joint surface 85.

As can be seen, the entire inner surface 86 and inner entrance valve chamber 87 is one smooth, seamless internal surface with no cap joint to collect debris.

Outer recesses 88 and 89 outward of diaphragm 90 are clearly depicted and act in exactly the same manner as recesses 37 and 38 shown in FIG. 1. Valve 79 is molded in one-piece of resilient 50 shore A durometer silicone.

Figure 8:
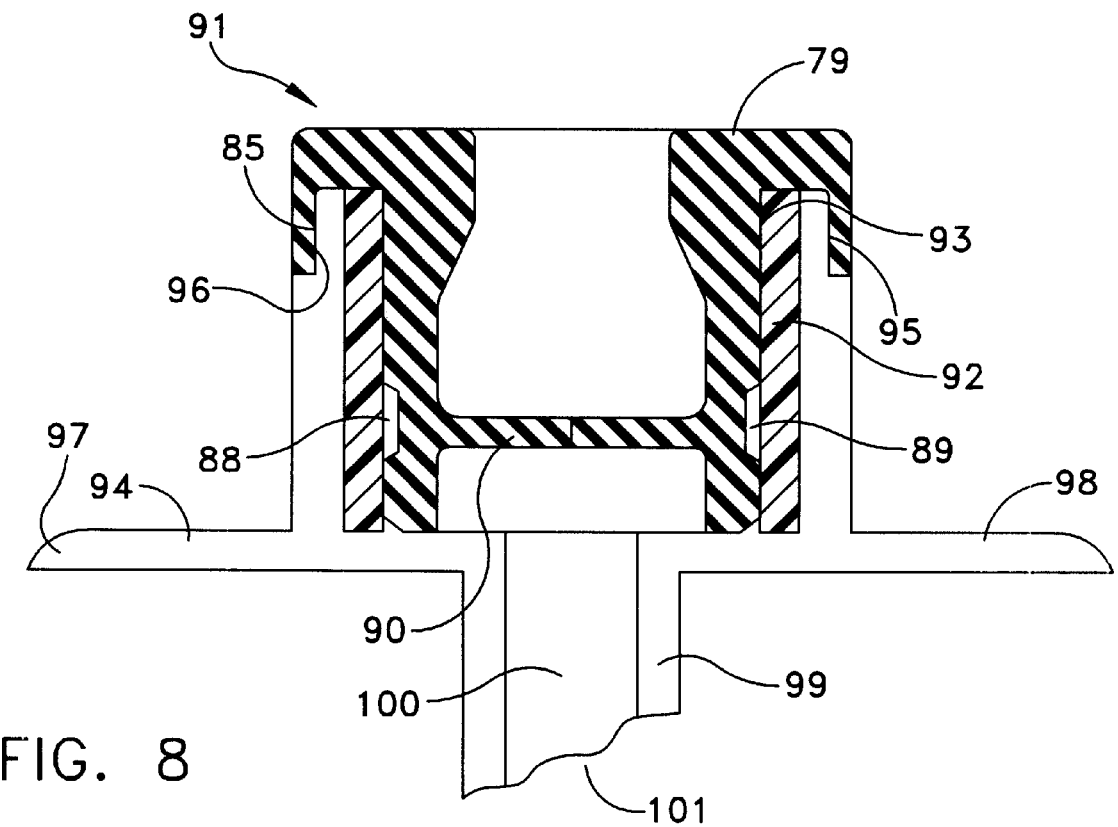
FIG. 8 is a partial cross sectional view of a low profile gastrostomy device utilizing the valve member depicted in FIG. 7.

FIG. 8 shows valve 79 incorporated into low profile gastrostomy device 91. Seamless internal valve 79 is first press fitted into rigid plastic molded housing 92 which acts in identical fashion on valve 79 as housing 12 acts on valve member 14 in FIG. 1. Recesses 88 and 89 on diaphragm 90 are permitted to flex outward and inward just like recesses 37 and 38 in FIG. 1.

Valve 79 which is press fit into housing 92 forms subassembly 93 which is conveniently joined to molded silicone external coupling 94 at joint 95. Joint 95 is a lap joint wherein silicone adhesive seals inner joint surface 84 on cap 80 to outer joint 96 on coupling 94.

Coupling 94 typically has outer flanges 97 and 98 which would rest down on the skin surface. As can be seen, the entire assembly above. Skin surface flanges 97 and 98 consists of only three components: valve 79, housing 92, and coupling 94 joined at one sealed external joint 95.

Tube 99 fits inside the body through the abdomen with inner flow passage 100 which can terminate at end 101 which can be any number of internal retaining tips inside the stomach.

The device 91 is so versatile in that it can be adapted to terminate in any type tip such as an inflatable balloon, pezzer style tip, cross bar type, or any desired tip which is desired.

Figure 9:
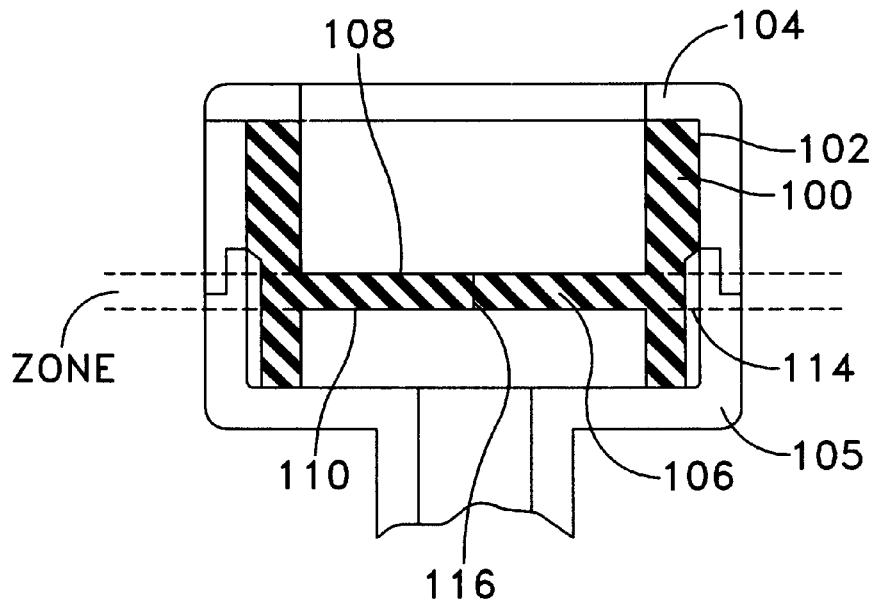
FIG. 9 is a partial cross-sectional view of another alternate embodiment.

FIG. 9 shows an embodiment similar to FIGS. 6 and 7 but where the valve member 100 is molded with a thicker upper wall 102 which contacts a cap 104 portion of the rigid housing so as to provide compression above diaphragm wall 106 in order to connect the valve member to the housing. The diaphragm wall as in the other embodiments includes parallel upper and lower spaced surfaces 108 and 110 which cooperate to define parallel planes which in turn define a zone 112 depicted by the dotted lines which extends across the assembly. It is important that the compression relief recess 114 be in such zone or at least a portion of such recess be located therein, that is, the compression relief recess should be proximal to the outer peripheral areas of the diaphragm wall and therefore prevent the compressive force created by an oversized dimensional relationship between the valve member outer walls and the housing inlet end cavity inner side walls from materially acting upon the diaphragm leaves. In other words, the recess 114 as well as the other compression relief recesses above and hereinafter described provide an area into which the peripheral areas of the diaphragm wall may, in effect, move into as when outward pressure is applied thereto as when a delivery set tip 54 is forced through the slit opening 116 formed in the diaphragm wall 106. A cap 118 similar to cap 16 shown in FIG. 1 but extending further downwardly is utilized to finish the assembly.

Figure 10:
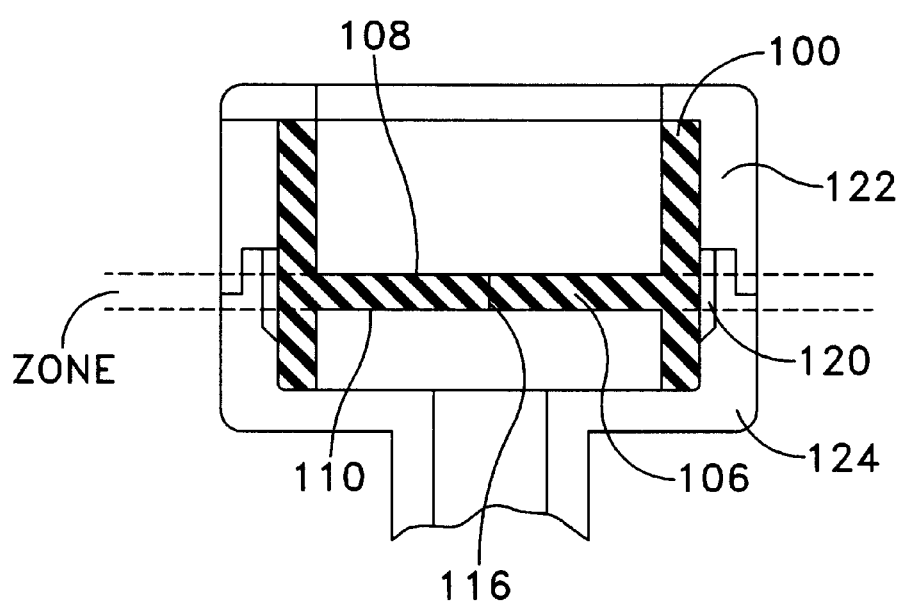
FIG. 10 is a partial cross-sectional view similar to FIG. 9 and shows still a further embodiment.

Similarly in FIG. 10, a compression relief recess 120 is defined by an outwardly extending recess formed as part of both the cap 122 and the housing 124 and although it could be impractical to mold, such recess could conceivably be entirely formed in the inner side wall of the housing inlet end cavity. In any case compression relief is achieved by positioning the relief recess both proximal to the outer peripheral areas of the diaphragm and in the above described zone although it should be pointed out that the recess can and does in most of the examples above shown extend further either above and/or below such zone.

Although the valve has been described for use in a long term indwelling catheter it is readily apparent that the valve or modifications thereof can be incorporated in a variety of other applications whether medical or commercial. It would therefore be apparent to those skilled in the art that many variations or modifications can be made without departing from the spirit and scope of the invention.

I claim:

1. A valve assembly comprising a housing having an inlet end, an outlet end and a connecting passageway therebetween, said inlet end including a cavity in turn having inner rigid side walls in contacting receipt of a resilient valve member, said valve member including a diaphragm portion with a slit therethrough and outer walls, a diaphragm wall laterally disposed between said valve outer walls and across said connecting passageway, said diaphragm wall including a slit, said slit defining opposed slit leaves each having a centrally disposed edge, said leaf edges in turn in normal sealing contact with each other so as to normally close said connecting passageway, said valve member outer walls generally conforming in shape to that of said inlet end cavity and dimensioned so as to have at least one portion thereof disposed distally from said diaphragm wall of an oversized greater dimension than said inlet end cavity whereby said valve member is compressed by said cavity inner side walls at said oversized portion but not compressed at valve member areas proximal said diaphragm wall so that such compression does not materially alter the normal sealing contact between said diaphragm leaves.

2. The valve assembly of claim 1, wherein said diaphragm wall has outer peripheral portions in turn connected to said valve member outer walls and wherein said valve member outer walls are inwardly recessed proximal to said diaphragm outer peripheral portions to a dimension less than that of said housing inlet cavity inner side walls adjacently positioned thereto.

3. The valve assembly of claim 1, wherein said inner side walls of said housing inlet cavity are outwardly recessed proximal to said diaphragm outer peripheral portions to a dimension greater than that of said valve member outer wall adjacently positioned thereto.

4. The valve assembly of claim 1, wherein said valve member is of one-piece construction and of a resilient elastomeric material.

5. The valve assembly of claim 1, wherein said diaphragm wall includes parallel spaced upper and lower surfaces which cooperatively form parallel planes which in turn define a zone which laterally extends across said assembly, and wherein said diaphragm wall has an outer peripheral area distal from the central area in which said slit is disposed and wherein there is a compression relief recess at least partially positioned in said zone and proximal to the outer peripheral area of said diaphragm wall.

6. The valve assembly of claim 5, wherein both said inlet cavity side walls and said valve member outer walls being circular and wherein said compression relief recess is in the form of a ring.

7. The valve assembly of claim 1, wherein said at least one portion of said valve member outer walls being of oversized dimension positioned above said diaphragm wall.

8. The valve assembly of claim 7, wherein there are two oversized dimensioned portions, one positioned above said diaphragm and the other positioned below said diaphragm.

* * * * *